United States Patent
Yamanashi et al.

[11] Patent Number: 5,964,759
[45] Date of Patent: *Oct. 12, 1999

[54] ELECTROCONVERGENT CAUTERY SYSTEM

[75] Inventors: William S. Yamanashi, Oklahoma City, Okla.; Arun Angelo Patil, Omaha, Nebr.

[73] Assignee: Ortho Development Corporation, Draper, Utah

[*] Notice: This patent is subject to a terminal disclaimer.

[21] Appl. No.: 08/837,365

[22] Filed: Apr. 17, 1997

Related U.S. Application Data

[63] Continuation-in-part of application No. 08/101,228, Aug. 3, 1993, which is a continuation-in-part of application No. 07/967,685, Oct. 27, 1992, abandoned.

[51] Int. Cl.⁶ .................................................. A61B 17/39
[52] U.S. Cl. ................................................. 606/52; 606/50
[58] Field of Search ........................... 606/34, 40, 41–42, 606/49–52

[56] References Cited

U.S. PATENT DOCUMENTS

| | | |
|---|---|---|
| 4,364,390 | 12/1982 | Shaw . |
| 4,752,673 | 6/1988 | Krumms . |
| 4,877,944 | 10/1989 | Cowell et al. . |
| 5,019,076 | 5/1991 | Yamanashi et al. . |
| 5,087,256 | 2/1992 | Taylor et al. . |
| 5,151,100 | 9/1992 | Abele et al. . |
| 5,159,584 | 10/1992 | Yanagida et al. . |
| 5,234,429 | 8/1993 | Goldhaber . |
| 5,278,809 | 1/1994 | Ogata . |
| 5,330,068 | 7/1994 | Rosar et al. ........................ 606/34 |
| 5,364,393 | 11/1994 | Auth et al. . |
| 5,423,810 | 6/1995 | Gobel et al. ........................ 606/40 |
| 5,425,731 | 6/1995 | Daniel . |
| 5,496,312 | 3/1996 | Klicek et al. ....................... 606/34 |

FOREIGN PATENT DOCUMENTS

| | | |
|---|---|---|
| 61-217903 | 9/1986 | European Pat. Off. . |
| 63-009001 | 1/1988 | European Pat. Off. . |
| 1-178104 | 7/1989 | European Pat. Off. . |
| 4-030303 | 2/1992 | European Pat. Off. . |
| 0576286A2 | 12/1993 | European Pat. Off. . |
| 9015409 | 12/1990 | WIPO . |

*Primary Examiner*—Linda C. M. Dvorak
*Assistant Examiner*—Roy Gibson
*Attorney, Agent, or Firm*—Clayton, Howarth & Cannon, P.C.

[57] ABSTRACT

A method for surgically treating tissue in a patient. The steps comprise touching a surgical tool to tissue that is to be surgically treated; heating the surgical tool by converging current to the tip of the surgical tool to create a high current density at the tip of the surgical tool so as to instantaneously vaporize the tissue being touched; and restricting the heat to the contact point on the tissue. The method eliminates the need for a solenoid coil and a grounding component.

26 Claims, 3 Drawing Sheets

ELECTROCONVERGENT CAUTERY SYSTEM

This is a continuation-in-part application of application Ser. No. 08/101,228 entitled "AN ELECTROCONVERGENT CAUTERY SYSTEM," filed Aug. 3, 1993, which is a continuation-in-part application of Ser. No. 07/967,685 entitled "AN ELECTROCONVERGENT CAUTERY SYSTEM," filed on Oct. 27, 1992, now abandoned.

BACKGROUND OF THE INVENTION

1. The Field of the Invention

This invention relates to an electroconvergent cautery system employing forceps or probes which produce sharply localized heating for cutting, vaporizing tissue and coagulating blood vessels when brought into contact with the same. More particularly, it concerns a method for using an electroconvergent cautery system.

2. The Background Art

Electrocautery systems are known in the art for coagulating vessels and for cutting tissue. Two common types of electrocautery systems are the monopolar and the bipolar systems. In the monopolar systems, high frequency electric current is passed from the cautery probe through the tissue to the grounding pad. Heat is generated in the tissue at the site of contact of the probe tip to the tissue. This heat is generated, by the flow current through the electrical resistance of the tissue in the preferred path between the probe tip contact site and the grounding pad. In such devices, the current is continuous sinusoidal or amplitude modulated. The monopolar system fails to provide uniform heating because tissue does not have uniform resistance and the tissue of lower resistance is the preferred path of current. For this reason, as the current flows from the point of contact of the probe to the surrounding tissue, heating tends to spread beyond the contact point of the probe to the surrounding tissue. This causes undesirable damage to the surrounding tissue. These problems of tissue damage were overcome by the bipolar system.

The bipolar system typically uses forceps to provide two tips. One tip is similar to the monopolar device and allows current to be supplied to the tissue while the other tip provides a return path for the current. By using two tips, the spread of current is limited to the path between the two tips and the current is prevented from spreading to the surrounding tissues and causing undesirable tissue damage. The monopolar and bipolar systems are able to cut tissue and coagulate vessels, but they cannot effectively vaporize tissue.

A lesion generator known as a radio frequency (RF) lesion generator is known in the art and works on the same principles as the monopolar cautery system except that a lower level of current is used and the current is of the continuous sinusoidal type. This current type results in more uniform tissue destruction. However, such a system is used exclusively for creating lesions.

In an effort to resolve the problems of the prior art, the inventors invented a method for using a radio frequency surgical tool which is disclosed in U.S. Pat. No. 5,019,076. This tool is capable of cutting and vaporizing tissue and coagulating vessels without the spread of heat to the surrounding tissue. In the device of said patent, a high frequency (13.56 or 27.0 MHz) current is passed through an amplifier, a matching network and a solenoid coil to generate an electromagnetic field. This in turn induces eddy currents in the tissue. Touching the tissue with a probe which is AC-coupled to a return circuit draws the eddy currents out of the tissue at the contact point of the probe producing intense heat which can cut and vaporize tissue as well as coagulate vessels. One disadvantage of the system of the said patent is that the proximity of the coil to the operative field causes inconvenience to the surgeon. A further disadvantage of the device of said patent is that the coagulating ability of the device is not as efficient as desired. Another disadvantage of the device is that it requires a grounding component.

Of current interest is a method for surgical treatment wherein a probe is used with an RF lesion generator to surgically treat tissue in a patient. This method overcomes the disadvantages of the prior art because the method provides means for surgical treatment using an RF generator without the necessity of a solenoid coil or a grounding component.

OBJECTS AND SUMMARY OF THE INVENTION

It is an object of the present invention to provide a method for using a monopolar electroconvergent cautery system to produce sharply localized heating for cutting tissue, vaporizing tissue and coagulating blood vessels when brought into contact with the same.

Another object of the present invention is to provide a method for using a monopolar electroconvergent cautery system to produce sharply localized heating for cutting tissue, vaporizing tissue and coagulating blood vessels when brought into contact with the same, the method eliminating the need of a solenoid coil in the operative field.

Yet another object is to provide a method for using a monopolar electroconvergent cautery system to produce sharply localized heating for cutting tissue, vaporizing tissue and blood vessels when brought into contact with the same, the method eliminating the need for a grounding component.

It is another object of the present invention to provide an electroconvergent cautery system which can coagulate blood vessels and cut and vaporize tissue without the spread of heat to the surrounding tissue.

It is another object of the invention, in accordance with one aspect thereof, to provide an electroconvergent cautery system utilizing surgical forceps having a pair of blades with one of the blades being a passive blade and other blade being an active blade.

It is another object of the invention, in accordance with one aspect thereof, to provide an electroconvergent cautery system including surgical forceps with the two blades thereof tapering towards their sharply pointed tips with the tip of the active blade being approximately 0.25 mm longer than that of the passive blade so that the tip of the former will touch tissue to cut and vaporize it without being obstructed from the surgeon's vision by the latter.

It is still another object of the invention, in accordance with one aspect thereof, to provide an electroconvergent cautery system with any size or shape of surgical forceps. another object of the invention, in accordance with one aspect thereof, is to provide an electroconvergent cautery system including laparoscopic forceps wherein the blades are short and the main stems thereof are long.

Still another object of the invention, in accordance with one aspect thereof, is to provide an electroconvergent cautery system including an endoscopic and endovascular probe with the probe consisting of a heavily insulated flexible or rigid wire having an exposed tip of approximately 5 mm with the distal end of the tip being sharply pointed with the tip either being straight, curved or angled.

Yet another object of the invention, in accordance with one aspect thereof, is to provide an electroconvergent cautery system including a laparoscopic probe the probe thereof being rigid and the tip being bent at a right angle.

Still another object of the invention, in accordance with one aspect thereof, is to provide an electroconvergent cautery system including a surgical probe comprised of a rigid wire with a tapered fine tip.

Still another object of the invention, in accordance with one aspect thereof, is to provide an electroconvergent cautery system including a lesion generating probe for ablation of various accessory pathways in the heart for arythmic patients.

The above objects and others not specifically recited are realized through an electroconvergent cautery system which is used as a surgical tool for coagulating blood vessels and cutting and vaporizing tissue.

Electrical current is passed through either a surgical probe or forceps. The current is generated by a radio frequency power generator which produces an alternating current of 13.56 or 27.0 MHz. An optional variable crest factor setting unit pulse modulates the sinusoidal to a variable interval square pulse of approximately 30 Hz–30 KHz and varies duty cycle and pulse height. An impedance matching device is utilized to match the impedance of the probe or the active blade of the forceps with the radio frequency power generator. A loading and tuning coil serves as an auto transformer or triggering means which minimizes the mismatch of impedance of the probe or the active blade of the forceps with the radio frequency generator upon touching the tip of the probe or the active blade of the forceps to the tissue. This causes the current to converge to the tip and results in high current density at the tip of the probe or the active blade of the forceps. Furthermore, the loading and tuning coil instantaneously causes the current at the probe tip to capacitatively couple with the return circuit drawing back the current into the return circuit. The high current density at the sharp tip of the probe or the active blade of the forceps produces intense localized heating which is capable of coagulating vessels and cutting and vaporizing tissue. When the probe is heated, current flow in the tissue is avoided and a high current density at the tip of the probe is heated. When vessels are held between the two tips of the forceps some energy is dissipated into the inactive blade resulting in diffuse heating which improves its coagulating property. Furthermore, while holding vessels between the two blades of the forceps, the contact of tissue is slightly proximal to the tip of the blade. This results in increased area of contact between the forceps and the tissue resulting in less intense and more diffuse heating which improves its coagulating property. A similar effect can also be achieved with the probe, by touching the tissue with the probe slightly proximal to its tip.

In the surgical forceps configuration, the two blades of the forceps, except for their tips, are insulated. The two blades at their proximal ends are separated by heavily insulated material. One of the blades serves as an active blade and is connected to the loading and tuning coil by means of a heavily insulated cable. The other blade of the surgical forceps is a passive blade and has no electrical connection. The two blades taper towards their sharply pointed tips with the tip of the active being approximately 0.25 mm longer than that of the passive blade. Any shape or size of existing surgical forceps may be connected to the system.

An endoscopic and endovascular probe is also disclosed which consists of a ⅝, ⅜, or ½ n wavelength long (wherein "n" is an integer) heavily insulated flexible or rigid wire with an exposed tip or required length. The distal end of the tip is sharply pointed with the tip being straight, curved or angled.

Also describe is a laparoscopic probe having a probe similar to the endoscopic probe except that the probe is rigid and the tip is bent at a right angle. Further described is a surgical probe comprised of a rigid wire with a tapered fine tip. Except for the exposed tip, the remainder of the probe is insulated with a pencil shaped configuration.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
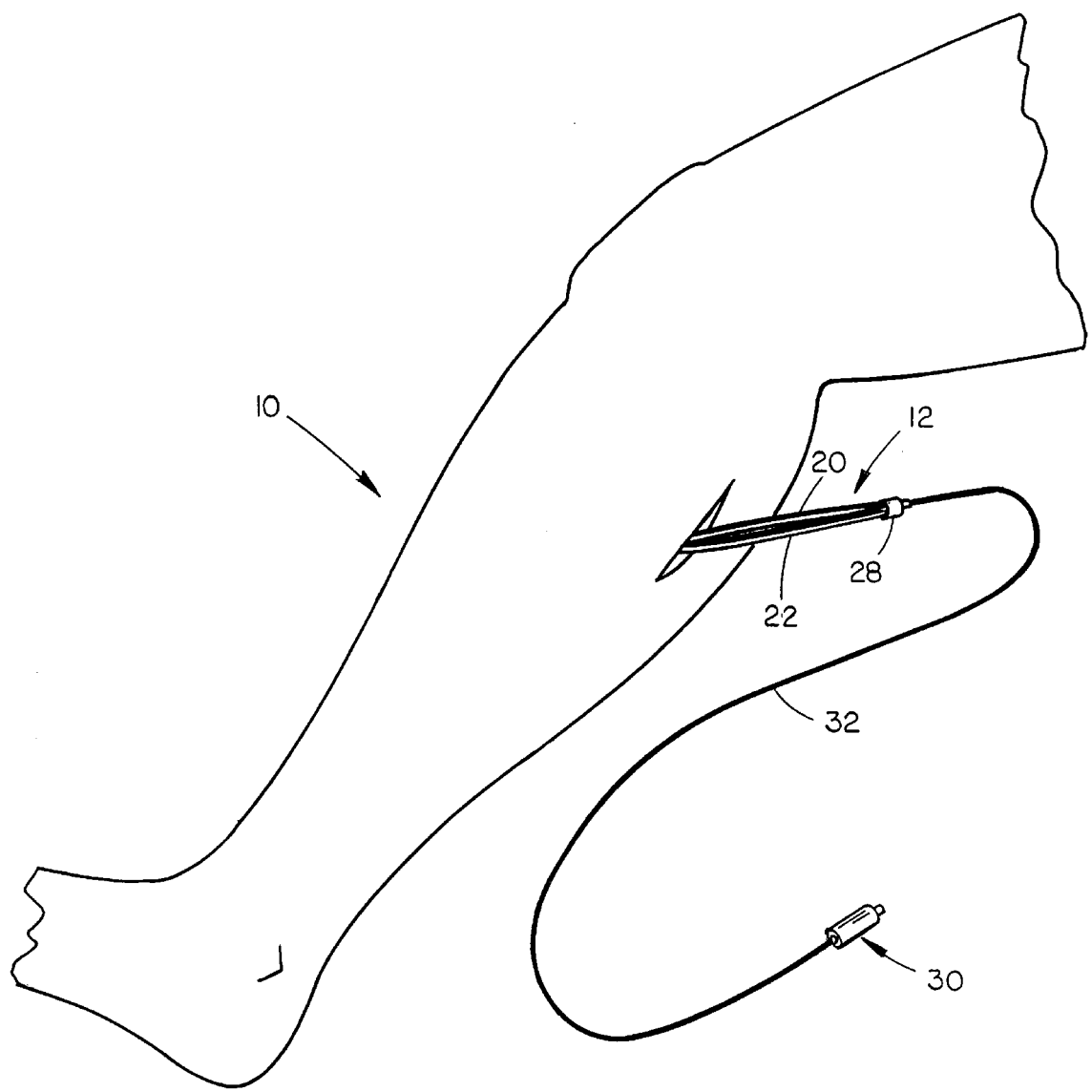
FIG. 1 is a perspective view of and form of an instrument utilized in the electroconvergent cautery system of this invention.
Figure 7:
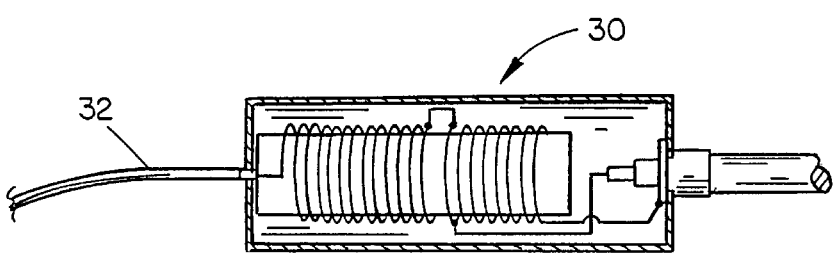
FIG. 7 is a sectional view of the loading and tuning coil of this invention.

Reference will now be made to the drawings wherein like structures will be provided with like reference numerals.

The present invention is directed to a method for using an electroconvergent cautery system. The method is for surgically treating tissue in a patient. The method involves the following steps:

a) selecting a surgical tool for contacting tissue that is to be surgically treated;

b) generating alternating current of a pre-selected frequency;

c) electrically coupling an impedance matching power source and control means with a power amplifier for matching the impedance of the surgical tool with a radio frequency generator;

d) placing the surgical tool in close proximity to tissue that is to be surgically treated;

e) identifying an impedance difference between the surgical tool and the impedance of the radio frequency generator; and f) heating the surgical tool by nullifying the impedance difference and converging current from the power source and control means to the surgical tool so that current flow in the tissue is avoided and a high current density at a tip of the surgical tool is created so as to instantaneously vaporize the tissue being touched.

The method is accomplished such that a grounding component and solenoid coil are unnecessary when a patient is treated. In addition, the method causes heat to be restricted to the contact point on the tissue because no current flows into the tissue. The contact point can be the point on the tissue where the surgical tool is brought in close proximity as mentioned above, or the contact point can be the point where tissue that is to be surgically treated is actually touched by the tip of the surgical tool.

The method described above is accomplished through the use of an electroconvergent cautery system. This system is shown in the figures. Referring to FIG. 1, the numeral 10 designates a human leg while the numeral 12 refers to a cautery instrument in the form of surgical forceps. A variety of cautery instruments are interchangeable in the electroconvergent cautery system such as the surgical forceps 14 in FIG. 3, laparoscopic forceps 16 in FIG. 4 and the surgical probe 18 illustrated in FIG. 5.

Figure 2:
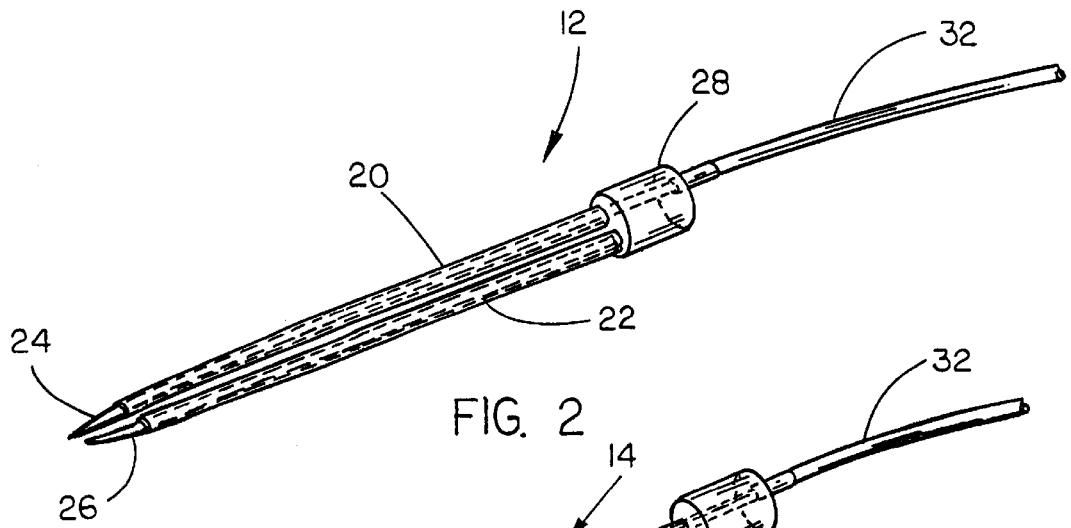
FIG. 2 is a perspective view of straight surgical forceps connected to an electric cable for use as an electroconvergent cautery instrument.

The surgical forceps 12 illustrated in FIG. 2 comprises a pair of straight blades 20 and 22 which are insulated except for the tips 24 and 26. Blades 20 and 22 are separated at their proximal ends by a heavily insulated material referred to by the reference numeral 28. Blade 20 serves as the active blade and is connected to the loading and tuning coil 30 by means of a heavily insulated cable 32. Blade 22 is passive and has no electrical connections. As seen in FIG. 2, blades 20 and 22 taper towards their sharply pointed tips. Tip 24 of the blade 20 is approximately 0.25 mm longer than the tip of the passive blade 22.

Figure 3:
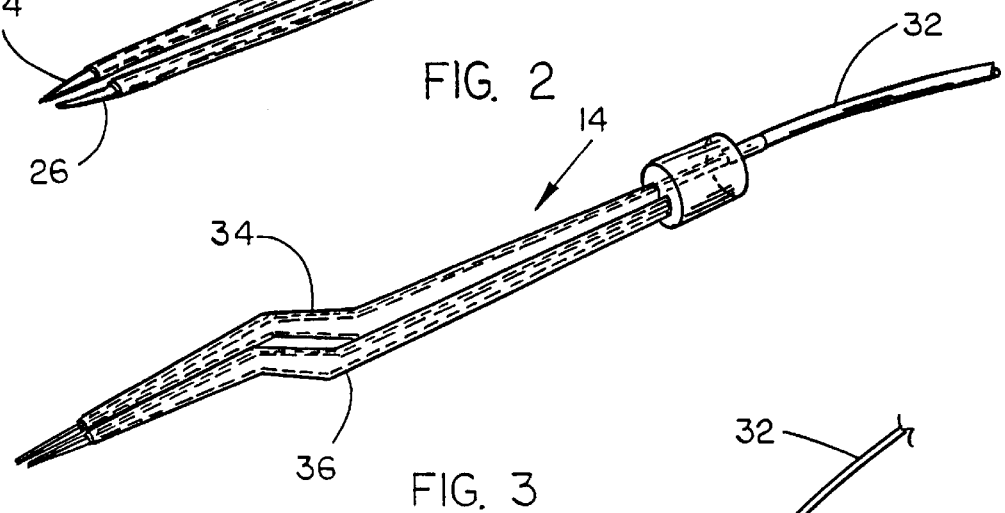
FIG. 3 is a view similar to FIG. 2 except that the forceps are bayonetted.

With respect to FIG. 3, the surgical forceps 14 illustrated therein are generally similar to the forceps shown in FIG. 2 except that the blades 34 and 36 are bayonetted. Blade 34 is the active blade and is electrically connected to the insulated cable 32. As in the surgical forceps 12, the tips of the active blade 34 is approximately 0.25 mm longer than that of the tip of the blade 36.

Figure 4:
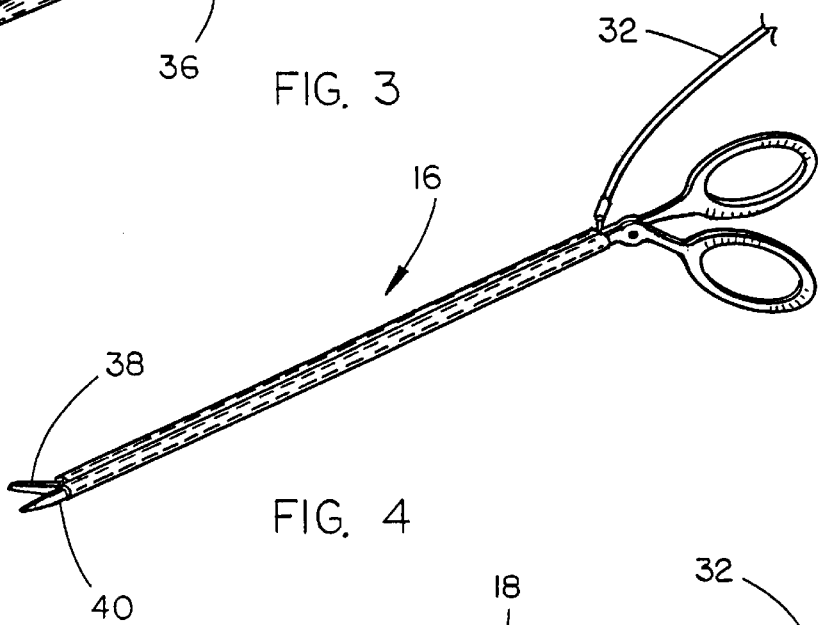
FIG. 4 is a perspective view of laparoscopic forceps similar to that shown in FIGS. 2 and 3 except that the blades are short and the main stems are long.

FIG. 4 illustrates a laparoscopic forceps which is similar to the surgical forceps of FIGS. 2 and 3 above except that the blades 38 and 40 are short with the main stems thereof being quite long. Blade 38 is operatively connected to the insulated cable 32.

Figure 5:
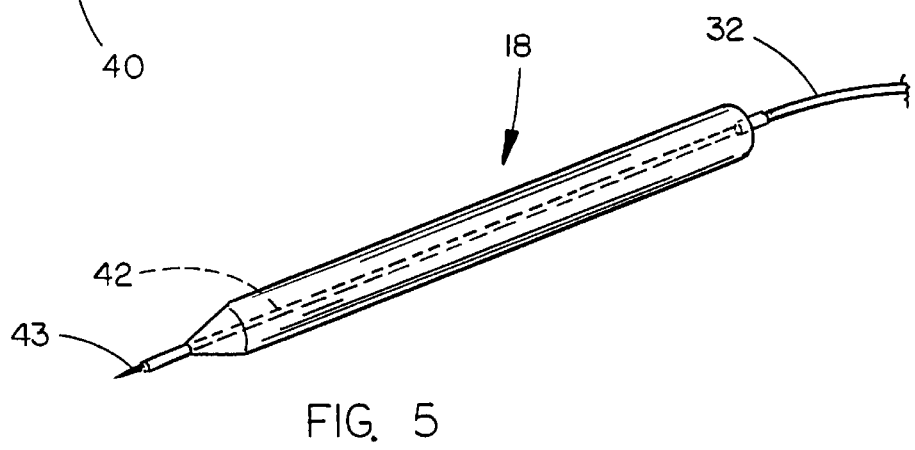
FIG. 5 is a perspective view of a surgical probe which may be used with the system of this invention.

The surgical probe 18 illustrated in FIG. 5 comprises a rigid wire 42 with a tapered fine tip 43. Except for approximately 5 mm of the tip 43, the remainder of the probe is insulated in a pencil shaped configuration for gripping purposes.

An endoscopic probe may also be provided which is generally similar to the surgical probe 18 of FIG. 5 except that the tip portion thereof may be straight, curved or angled. The outer diameter of the probe would be a multiple of the wavelength of the current flowing therein and may be rigid or flexible. This probe may be used as a resectoscope or as an endovascular probe. Further, the probe could have its tip bend at a right angle.

Figure 6:
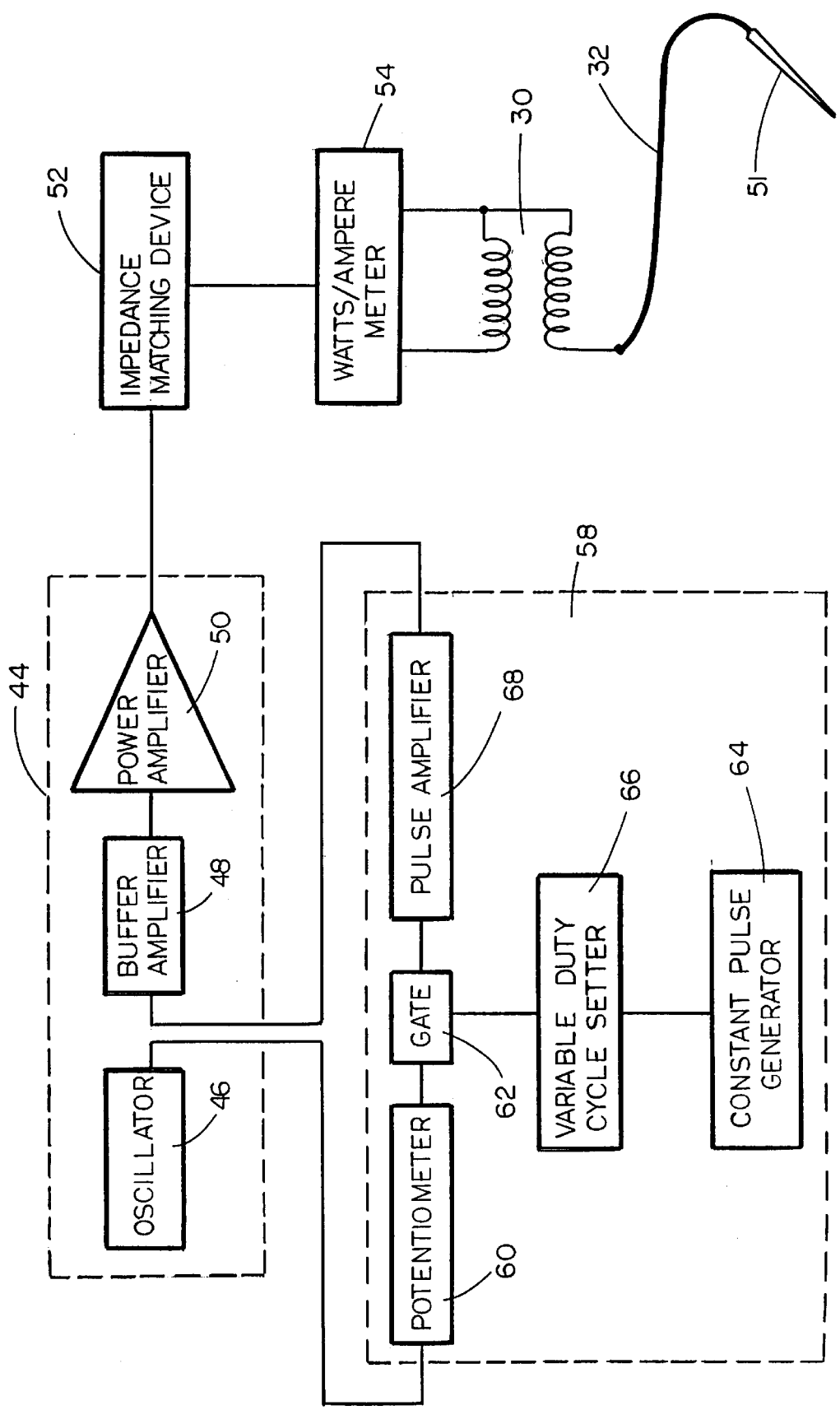
FIG. 6 is a schematic of the electrical circuitry of the system.

FIG. 6 shows a complete electroconvergent cautery system in block diagram form. The numeral 44 refers to a radio frequency power generator which comprises an oscillator 46, buffer amplifier 48 and power amplifier 50. As seen in FIG. 6, an impedance matching device 52 is electrically connected to the radio frequency power generator. A watts/ampere meter 54 is electrically connected to the radio frequency power generator. The watts/ampere meter 54 can be electrically connected to the impedance matching device 52 and is electrically connected to the loading and tuning coil 30. The loading and tuning coil 30 is connected to the surgical instrument 51 by means of the heavily insulated cable 32. As stated, the surgical instrument 51 may be comprised of those instruments previously described. The cable 32 connects the surgical instrument 51 to the loading and tuning coil 30 as described. The combined lengths (sum) of the cable 32 and the probe is a multiple of the current.

A variable crest factor setting unit 58 is interposed between the oscillator 46 and the buffer amplifier 48. The variable crest factor setting unit 58 is comprised of a peak voltage setting potentiometer 60, a gate 62, a constant pulse generator 64, a variable duty cycle setter 66 and a pulse amplifier 68.

The RF power generator 44 can generate an alternating current of various frequencies. Due to federal regulations, the preferred frequencies are 13.56 or 27 MHz. The variable crest factor setting unit 66 varies duty cycle and pulse height and is used to modulate the waveform. Although the waveform can be modulated into numerous forms, the currently preferred form is a continuous square wave of approximately 30 Hz–30 KHz. The impedance matching device 52 matches the impedance of the probe or forceps with the RF generator 44. The loading and tuning coil 30 together serves as an autotransformer. When the probe tip touches the tissue, the mismatch of impedance between the probe and the radio frequency generator is nullified resulting in high current density at the tip of the probe or the active blade of the forceps which in turn results in high temperature at the contact point. Furthermore, the loading and tuning coil causes the current at the probe tip to capacitively couple with the return circuit. Therefore, touching the sharp tip of the probe the active blade of the forceps to the tissue produces sharply localized heating which can cut and vaporize tissue. When vaporizing or cutting tissue, the active blade touches the tissue due to its longer length. Furthermore, when the vessels are held between the two tips of the forceps, the contacted tissue is slightly proximal to the tip. Such results in an increased area of contact between the forceps and the tissue resulting in less intense and more diffuse heating than a single top prove, which is ideal for coagulation. A similar effect can also be achieved by touching the tissue with the probe slightly proximal to its tip.

The electroconvergent cautery system can also be used in a method for vaporizing, cutting and/or cauterizing tissue. This method includes the following steps:

obtaining a probe tip for treating tissue in a surgical procedure;

placing the probe tip in close proximity to the tissue to be treated in the surgical procedure;

generating an alternating current waveform having a pre-selected frequency, the alternating current waveform being generated by a power generator;

measuring a difference in impedance between the probe tip and an output of the power generator; and any impedance difference between the probe tip and the output of the power generator by converging current from the generator to the probe tip, thereby heating the probe tip.

Like the first method disclosed in this application, the above method is accomplished without a grounding component and a solenoid coil. In addition, the step of placing the probe tip in close proximity to the tissue to be treated in the surgical procedure involves either bringing the probe tip close to the treatment tissue or actually touching the probe tip to the treatment tissue.

Thus, it can be seen that the invention accomplishes at least all of the stated objectives.

The above variations are not inclusive. They are only examples of the preferred embodiments. It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A method for surgically treating tissue in a patient comprising the steps of:
   a) selecting a surgical tool for contacting tissue that is to be surgically treated;
   b) generating alternating current of a pre-selected frequency with a radio frequency generator;
   c) electrically coupling an impedance matching power source and control means with a power amplifier for matching the impedance of the surgical tool with the radio frequency generator;
   d) placing the surgical tool in close proximity to tissue that is to be surgically treated;
   e) identifying an impedance difference between the surgical tool and the impedance of the radio frequency generator; and
   f) heating the surgical tool by nullifying the impedance difference and converging current from the power source and control means to the surgical tool so that current flow in the tissue is avoided and a high current density at a tip of the surgical tool is created so as to instantaneously vaporize the tissue being touched.

2. The method of claim 1 wherein the step of heating the surgical tool comprises heating the surgical tool without using a grounding component and a solenoid coil.

3. The method of claim 1 further comprising the step of restricting the heating of the surgical tool to the contact point on the tissue.

4. The method of claim 1 wherein the step of placing the surgical tool in close proximity to tissue that is to be surgically treated further comprises touching the tip of the surgical tool to tissue that is to be surgically treated.

5. The method of claim 1 wherein the step of generating alternating current of a pre-selected frequency comprises using a pre-selected frequency of 13.56 MHz.

6. The method of claim 1 wherein the step of generating alternating current of a pre-selected frequency comprises using a pre-selected frequency of 27 MHz.

7. The method of claim 1 wherein the step of generating alternating current of a pre-selected frequency comprises modulating a waveform created by the radio frequency power generator to a continuous square wave.

8. The method of claim 7 wherein the step of generating alternating current of a pre-selected frequency comprises using a radio frequency power generator having a variable crest factor setting unit, the variable crest factor setting unit having a series coupled potentiometer, a gate, and a pulse amplifier, the gate being series coupled to (i) a variable duty cycle setter and (ii) a constant pulse generator.

9. The method of claim 1 wherein the step of selecting a surgical tool comprises selecting a surgical forceps.

10. The method of claim 9 wherein the step of selecting a surgical forceps comprises selecting a surgical forceps having two blades, the two blades having sharply pointed tapering tips.

11. The method of claim 9 further comprising the step of:
    contacting the surgical forceps to tissue that is to be surgically treated; and
    holding the tip of the forceps slightly proximal to contacted tissue so that, compared to a single tip probe, an increased area of contact between the forceps and the tissue results thereby causing less intense and more diffuse heating than the single tip probe.

12. The method of claim 1 wherein the step of selecting a surgical tool comprises selecting a probe that has the configuration of one blade of a surgical forceps.

13. The method of claim 1 wherein the step of selecting a surgical tool comprises selecting a probe that is a wire.

14. The method of claim 1 wherein the step of selecting a surgical tool comprises selecting a probe that is a knife.

15. The method of claim 3 wherein the step of restricting the heat to the contact point on the tissue comprises capacitatively coupling the current at the surgical tool with a return circuit.

16. A method for vaporizing, cutting and/or cauterizing tissue comprising the steps of:
    obtaining a probe tip for treating tissue in a surgical procedure;
    placing the probe tip in close proximity to the tissue to be treated in the surgical procedure;
    generating an alternating current waveform having a pre-selected frequency, the alternating current waveform being generated by a power generator;
    measuring a difference in impedance between the probe tip and an output of the power generator; and
    nullifying any impedance difference between the probe tip and the output of the power generator by touching the tissue with the probe tip and converging current from power generator to the probe tip, thereby heating the probe tip.

17. The method of claim 16 wherein the step of nullifying any impedance difference comprises heating the probe tip without using a grounding component and a solenoid coil.

18. The method of claim 16 wherein the step of placing the probe tip in close proximity to the tissue to be treated in the surgical procedure comprises touching the probe tip to the tissue to be treated.

19. The method of claim 16, wherein the step of obtaining a probe tip comprises selecting an endoscopic probe.

20. The method of claim 16 wherein the step of obtaining a probe tip comprises selecting a lesion generating probe for ablation of various accessory pathways in the heart for arythmic patients.

21. The method of claim 16 wherein the step of nullifying any impedance difference comprises capacitatively coupling current at the probe tip with the return circuit drawing back the current into the return circuit.

22. The method of claim 16 wherein the step of nullifying any impedance difference comprises generating high current density at the tip of the probe.

23. Apparatus for vaporizing, cutting and/or cauterizing tissue, comprising:
    a probe tip for treating tissue in a surgical procedure;
    a loading and tuning coil connected in series with the probe tip;
    a watts/ampere meter connected in series with the loading and tuning coil;
    an impedance matching device connected in series with the watts/ampere meter and including means for nullifying detected impedance differences; and a power generator connected in series with the impedance matching device for generating an alternating current of a preselected frequency;

said loading and tuning coil being operable as a triggering means for sensing the presence of tissue to be cauterized without use of a grounding component or a solenoid coil and for heating the probe tip by nullifying an impedance difference between the probe tip and the power generator.

24. A method for surgically treating tissue in a patient comprising the steps of:

a) selecting a surgical tool for contacting tissue that is to be surgically treated;

b) generating alternating current of a pre-selected frequency with a radio frequency generator;

c) electrically coupling an impedance matching sower source and control means with a sower amplifier for matching the impedance of the surgical tool with the radio frequency generator;

d) placing the surgical tool in close proximity to tissue that is to be surgically treated;

e) identifying an impedance difference between the surgical tool and the impedance of the radio frequency generator;

f) heating the surgical tool by nullifying the impedance difference and converging current from the Power source and control means to the surgical tool so that current flow in the tissue is avoided and a high current density at a tip of the surgical tool is created so as to instantaneously vaporize the tissue being touched; and a) wherein the step of selecting a surgical tool comprises selecting a laparoscope forceps having blades and main stems, wherein the blades are short and the main stems thereof are long.

25. A method for surgically treating tissue in a patient comprising the stems of:

a) selecting a surgical tool for contacting tissue that is to be surgically treated;

b) generating alternating current of a pre-selected frequency with a radio frequency generator;

c) electrically coupling an impedance matching sower source and control means with a sower amplifier for matching the impedance of the surgical tool with the radio frequency generator;

d) placing the surgical tool in close proximity to tissue that is to be surgically treated;

e) identifying an impedance difference between the surgical tool and the impedance of the radio frequency generator;

f) heating the surgical tool by nullifying the impedance difference and converging current from the power source and control means to the surgical tool so that current flow in the tissue is avoided and a high current density at a tip of the surgical tool is created so as to instantaneously vaporize the tissue being touched; and g) wherein the step of selecting a surgical tool comprises selecting an endoscopic probe, the probe being rigid and having a tip, the probe having means to bend the probe tip at a right angle.

26. A method for surgically treating tissue in a patient comprising the steps of:

a) selecting a surgical tool for contacting tissue that is to be surgically treated;

b) generating alternating current of a pre-selected frequency with a radio frequency generator;

c) electrically coupling an impedance matching power source and control means with a power amplifier for matching the impedance of the surgical tool with the radio frequency generator;

d) placing the surgical tool in close proximity to tissue that is to be surgically treated;

e) identifying an impedance difference between the surgical tool and the impedance of the radio frequency generator;

f) heating the surgical tool by nullifying the impedance difference and converging current from the power source and control means to the surgical tool so that current flow in the tissue is avoided and a high current density at a tin of the surgical tool is created so as to instantaneously vaporize the tissue being touched; and g) wherein the step of selecting a surgical tool comprises selecting a lesion generating probe for ablation of various accessory pathways in the heart for arythmic patients.

* * * * *